United States Patent [19]

McIntyre et al.

[11] Patent Number: 4,762,517
[45] Date of Patent: Aug. 9, 1988

[54] SUBCUTANEOUSLY-IMPLANTED DRUG DELIVERY SYSTEM FOR INTRAVENOUS INJECTIONS, AND THE LIKE

[75] Inventors: Jeffrey A. McIntyre; Timothy P. Cadieux, both of Chicago, Ill.

[73] Assignee: Healthcare Technologies, Inc., Skokie, Ill. ; by said Timothy P. Cadieux

[21] Appl. No.: 909,002

[22] Filed: Sep. 18, 1986

[51] Int. Cl.⁴ ............................................. A61M 5/00
[52] U.S. Cl. ..................................... 604/175; 604/283; 128/DIG. 26
[58] Field of Search ............... 604/175, 174, 280, 283, 604/93; 128/DIG. 26

[56] References Cited

U.S. PATENT DOCUMENTS

| | | | |
|---|---|---|---|
| 4,190,040 | 2/1980 | Schulte | 128/1 R |
| 4,405,305 | 9/1983 | Stephen et al. | 604/49 |
| 4,464,178 | 8/1984 | Dalton | 604/174 |
| 4,569,675 | 2/1986 | Prosl et al. | 604/175 |

FOREIGN PATENT DOCUMENTS 0141625  5/1985  European Pat. Off. .

OTHER PUBLICATIONS

"PORT-A-CATH—Guidelines for Implantation," by Pharmacia Inc. © 1984.
"PORT-A-CATH—Use and Maintenance Procedures," by Pharmacia Inc. © 1984.

Primary Examiner—C. Fred Rosenbaum
Assistant Examiner—Gene B. Kartchner
Attorney, Agent, or Firm—Milton S. Gerstein; Marvin Benn

[57] ABSTRACT

A subcutaneously-implanted infusion device that has a portal defining an inner reservoir chamber that allows communication between a septum and an end of a catheter tube connected to the portal. The septum is mounted in a compressed state within a main housing of the portal by a pressure-insert element that is formed against the septum by an arbor press. The septum is then held in its compressed state via a retaining ring cooperating with an annular groove provided in the interior surface of the main housing directly adjacent the lower end of the portal. The device also includes a lower suture-attaching cuff having a skirt portion, with a low profile angle, which is provided with a plurality of separate, spaced-apart, suture-reinforcing tabs. The pressure-insert element is provided with a through-hole for the passage of a catheter with an enlarged abutment stop at one end for preventing passage of the catheter through the through-hole. Medical glue to used to bond the end of the catheter to the interior surface of the pressure-insert element. A protective metal sleeve is mounted about the portion of the catheter directly adjacent the outer circumference of the pressure-insert element for protecting against accidental puncture of the portion of the catheter which extends from the through-hole.

17 Claims, 1 Drawing Sheet

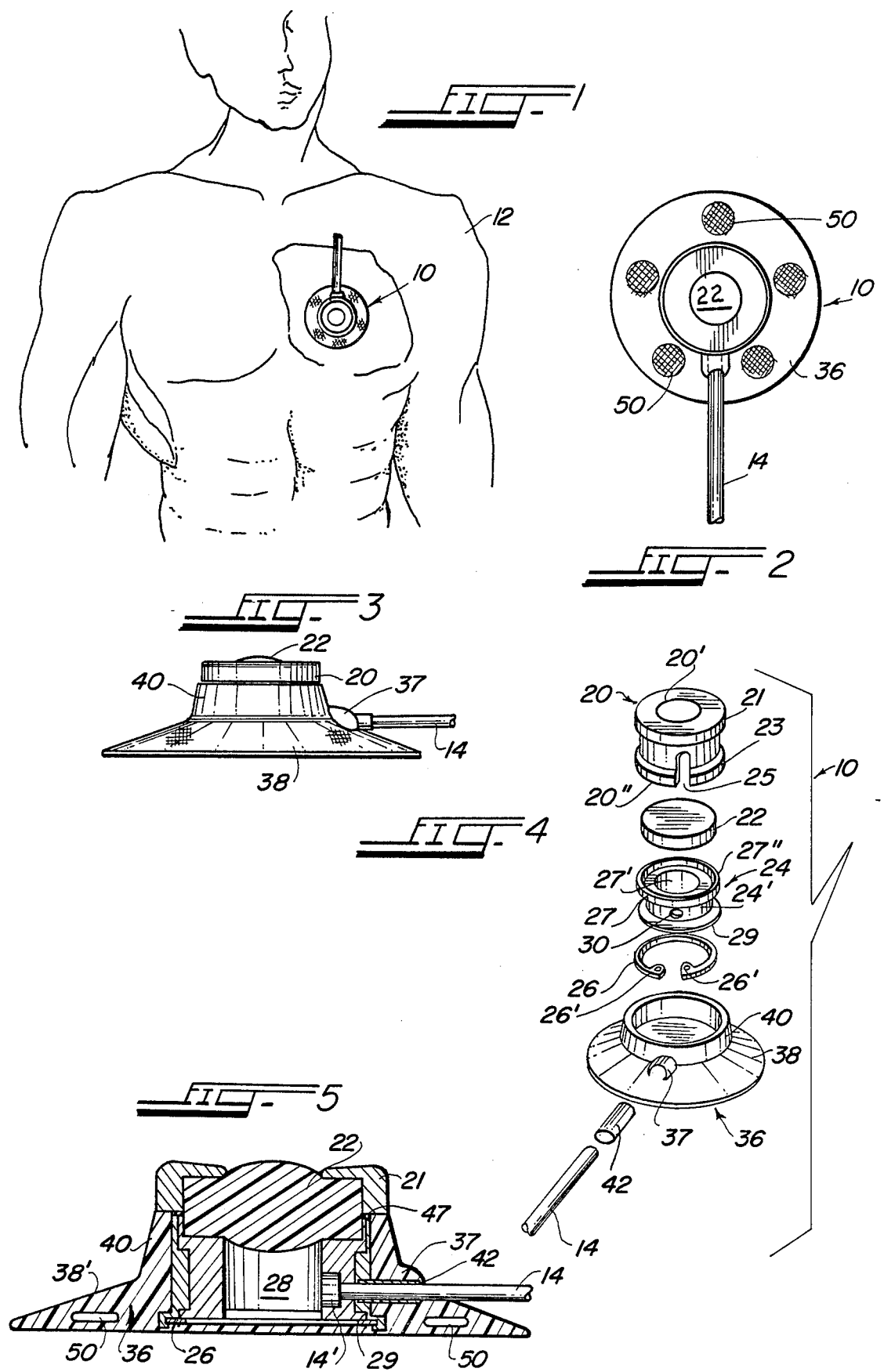

SUBCUTANEOUSLY-IMPLANTED DRUG DELIVERY SYSTEM FOR INTRAVENOUS INJECTIONS, AND THE LIKE

BACKGROUND OF THE INVENTION

The present invention is directed to a drug delivery system that is subcutaneously-implanted for repeated intravenous, intra-arterial or intraperitoneal injections or infusions into the human bloodstream of drugs, antibiotics, parenteral products, blood, therapeutic agents, and the like. The system may also be used for the withdrawal of blood samples from the patient. The subcutaneously-implanted delivery system allows for up to 2000 needle penetrations, with a non-coring 22-gauge needle, to the artery or vein, without having to access the artery or vein directly, thereby considerably increasing patient comfort, as well as eliminating the hitherto high risk of infection and thrombosis due to repeated venipuncture. Furthermore, extravasation of some drugs is also eliminated, as well as the time expended by medical personnel in the search for a suitable vein to deliver drugs, or the like, to the patient. The subcutaneously-implanted delivery system also allows for regionalized therapy, and the system does not interfere with the patient's normal routine, since there are no exterior components which could be damaged through daily activities of the patient.

When the subcutaneously-implanted delivery system is to be used as an intravenous system, the system's catheter is typically inserted into the superior vena cava, or right atrium, through the subclavian vein or internal jugular vein, with the portal, or main housing of the system, placed over the patient's third or fourth rib. For intraarterial delivery, the catheter is usually inserted into the hepatic artery and the portal, or main, housing placed over the patient's lower ribs. For intraperitoneal delivery, the catheter is inserted into the peritoneal cavity via a small incision on either side of the umbilicus. The catheter tip is then placed to the right or left of the pelvic gutter prerectally. In this instance, the portal housing of the system is also usually implanted over the lower ribs. In each case, the portal housing is implanted and sutured to the muscle fascia at the appropriate site.

The delivery system includes the portal housing, which also includes a self-sealing septum through which a non-coring needle is inserted to a depth which penetrates the septum and into the reservoir chamber of the portal housing, which is in fluid cooperation with an end of the catheter communicating with the reservoir chamber. The catheter is connected at its other end to the particular and appropriately-chosen vein or artery. For injection or infusion, the drug or fluid being administered flows from the needle through the reservoir chamber of the portal housing, and then through the catheter directly into the vein, artery or peritoneal cavity. The non-coring needle is provided with a very sharp deflected point, thus preventing coring or removal of a portion of the septum upon penetration and removal, thus allowing for repeated injections with as many as 2,000 punctures using a 22-gauge needle. The system is, therefore, especially suitable for therapy involving numerous administrations of a multitude of drugs, such as in chemotherapy regimens. The fluids that may be transported through the portal housing, and through the catheter to the bloodstream, are drugs such as antineoplastics, antibiotics, whole blood products, red blood cell products, any many other fluids. At the same time, of course, blood samples may be taken by the same process. Studies have shown that there is considerably fewer instances of infection, sepsis, and catheter occlusion since only the septum is accessed, and the vein or artery is accessed only once.

Examples of prior art subcutaneously-implanted delivery systems are: U.S. Pat. Nos. 4,190,040; 4,405,305; 4,464,178; and 4,569,675. In all prior art implanted delivery systems, it is essential that the septum be force-fitted into the portal or main housing such that there is no likelihood of it coming loose and allowing air into the system. It is also essential that the silicone septum, mounted in the portal housing, be compressed in order to allow for the maximum number of punctures of the septum, with the preferred being over 2,000. Also, conventional systems require extremely close tolerances because the stainless steel parts are press-fitted, or are assembled in three pieces with mating thread connections. In these prior art products, the percentage of rejects due to improper sealing of the interior reservoir chamber is unacceptably large. Further, these prior art products can, with time, pose serious problems with leakage from the interior reservoir chamber connecting the septum to the catheter. In addition, the number of critical tolerances in prior art products are considerable because of the number of parts used and the surface areas involved. For these reasons, the present invention is directed to minimizing tolerance requirements and the number of parts requiring such close tolerances, and for reducing the number of parts, per se, in the portal housing as well as the structure for compressing the septum in the interior of the housing above the reservoir chamber, all of which lead to considerable ease in manufacture, compared to prior art techniques and products, as well as enhanced and improved efficiency of the product itself. While the product of the present invention, as used in its implanted state, is used substantially similar to prior art products, it offers a safer, more easily handled, and more comfortable subcutaneously-implanted fluid delivery system, whether for intravenous, intra-arterial or interperitoneal delivery.

SUMMARY OF THE INVENTION

It is, therefore, the primary objective of the present invention to provide a subcutaneously-implanted infusion system that is relatively easy to manufacture, without the requirement of many close tolerances and with the minimum number of parts requiring tolerances.

It is also a primary objective of the present invention to provide such a system that is safer to use, and which allows for a greater number of punctures through the septum thereof than the products previously provided in the prior art.

It is another objective of the present invention to provide such subcutaneous infusion system in which the septum thereof is compressed such that the likelihood of air penetrating the reservoir chamber below the septum is minimal, as compared to prior art products.

It is another objective of the present invention to provide separately-defined suture grids or tabs embedded in the silicone attaching cuff of the infusion system, which grids allow for suturing the device to the muscle fascia in an easier manner which, also, assures proper implantation of the device of the present invention.

It is also an objective of the present invention to provide a protective metal sleeve about the end of the catheter attached to the portal housing in order to prevent accidental penetration of a needle of a syringe through the catheter.

Toward these and other ends, the subcutaneously-implanted infusion device of the present invention includes a portal, which defines therein a reservoir cavity which allows communication between the end of the catheter connected to the portal housing and the septum. The portal includes a first, hollow, cylindrical main housing having a first open end having an enlarged opening, and a second open end having a relatively smaller opening. The second open end of the portal is provided for the projection therethrough of the top surface of the septum. The septum itself is mounted in the interior of the hollow main housing at the end thereof adjacent the smaller opening of the second open end. The second main piece of the portal is a reel-like, pressure-insert element having a main cylindrical portion and a pair of projecting end flanges for insertion in the main housing, such that one end flange thereof is in abutting relationship with the bottom surface of the septum facing toward the larger opening of the first end of the main housing. The reel-like member also has a hollow interior, with one end thereof being closed and the second end thereof being open, so that the interior thereof defines the reservoir chamber, allowing for the communication between the end of the catheter connected to the portal with the septum itself, so that a needle injected through the septum may be in fluid communication with the end of the catheter. The end of the reel-like member that is closed is substantially flush with the larger opening of the first end of the main housing, where there is provided an inner circular retaining groove, which receives therein a C-shaped retaining ring, so that the reel-like member is kept forced against the septum, thereby compressing it and thereby providing a leakproof seal in the inner chamber of the cylindrical main housing. The septum is compressed via the reel-like member by an arbor press to the desired compression ratio, at which time the retaining ring is inserted, by an appropriate tool, into the circular retaining groove. After the retaining ring has been inserted into the retaining groove, to thereby establish the fixed state of compression of the septum, the arbor press is removed and the portal is complete.

The reel-like member is also provided with a through-opening along a portion of its circumferential surface between the end flanges, which through-opening allows for the insertion of one end of the catheter, which end is subsequently affixed to a vein, artery, or other infusion area, depending on its use. The other end of the catheter is provided with an enlarged beaded portion for the prevention of the other end of the catheter passing through the through-opening of the reel-like member, to thereby provide the means by which the end of the catheter is in fluid communication with the reservoir chamber of the portal. The outer, cylindrical main housing is also provided with a transverse slot that cooperates with the through-opening of the reel-like member to allow for the projection of the catheter therethrough, and eventually for the connection of the one end of the catheter to the artery or vein. After the other end of the catheter has been held in place against the inner surface of the reservoir chamber of the portal's reel-like member, the other end is fixedly connected in non-movable fashion to the interior surface of the reel-like member via the application of medical glue. The extension of the catheter through the through-opening of the reel-like member of the portal is carried out prior to the assembly of the parts of the portal described above.

After the sub-assembly of the portal is achieved, the silicone cuff is formed about the lower region of the portal by placing the sub-assembly of the portal in a suitably provided mold, after which liquid silicone is injected to a height such that the upper lip of the subsequently-formed silicone cuff of the device is approximately one-third of the distance away from the smaller opening of the second end of the main housing of the portal. After the silicone has been poured into the mold, a plurality of circular, separate, reinforcing synthetic, polyester fiber tabs, such as "Dacron," are inserted into the liquid silicone and embedded therein approximately one-half the distance between the top and bottom surfaces of the liquid silicone, which Dacron tabs provide the reinforcing mesh for the application of the sutures for mounting the portal to the patient's muscle fascia. The mold lid is thereafter placed on the mold and the entire mixture is allowed to cure for up to 24 hours, after which the excess silicone is trimmed, and the upper lip of the thus-formed hardened silicone is medically glued to the adjacent underlapping outer surface portions of the cylindrical main housing of the portal, for preventing the separation of the silicone cuff from the remainder of the portal.

There is also provided a protective metal stainless steel sleeve adjacent the other end of the catheter, which protective sleeve is encased in a bubble during the molding process. The stainless steel protective sleeve protects the end-portion of the catheter adjacent the portal such that accidental puncture of the end-portion of the catheter by the needle of a syringe is prevented. The plurality of Dacron reinforcing circular tabs are an improvement over the prior art process of providing a continuous Dacron annular strip, extending 360 degrees around the silicone cuff, which Dacron annular strip was difficult to insert into the liquid silicone in an even and level manner. The silicone cuff of the invention also has an angular profile substantially less than prior art products, which allows for ease when inserting the sutures therethrough, as opposed to prior art products, since the needle penetrates a thinner amount of silicone. The silicone cuff completely surrounds both the bottom portion of the housing, at which is located the retaining ring, and extends upwardly a majority of the outer surface of the main housing of the portal.

BRIEF DESCRIPTION OF THE DRAWINGS

The invention will be more readily understood with reference to the accompanying drawings, wherein:

FIG. 1 is a perspective view showing the subcutaneously-implanted infusion device of the present invention, implanted in a patient;

FIG. 2 is a plan view of the subcutaneouslyimplanted infusion delivery system of the invention;

FIG. 3 is a side elevational view of the subcutaneously-implanted infusion device of the invention;

FIG. 4 is an assembly view, in perspective, showing the arrangement of parts of the portal of the subcutaneously-implanted infusion device of the invention; and FIG. 5 is a cut-away view, in partial cross section, of the device of the invention.

DETAILED DESCRIPTION OF THE DRAWINGS

Referring now to the drawing in greater detail, the subcutaneously-implanted infusion device is indicated generally by reference numeral 10. The device 10 is implanted, subcutaneously, and fastened to the muscle fascia of a patient 12 so that the catheter 14 may be connected at a first end, in a conventional manner, to a vein or artery. The device 10 is shown in detail in FIGS. 4 and 5, and is made up of a portal formed by the parts indicated by reference numerals 20, 22, 24 and 26. The part 20 is a substantially hollow, cylindrical, main housing having a pair of end flanges 21 and 23 defining thereat end openings 20' and 20" of the housing. The opening 20' is of smaller diametric extension than the opening 20", with the opening 20' constituting the opening through which a portion of the upper surface of the septum 22 projects through the housing, through which septum is inserted a needle of a syringe for accessing the reservoir chamber of the portal. The housing 20 also includes a transverse slot or groove 25, having a closed end and an open end, which open end merges with the enlarged open end 20" of the housing 20. The groove or slot 25 is used to accommodate the end of the catheter 14 connected to the portal, as described below in greater detail.

The part 24 is a reel-like pressure-insert element having a main cylindrical portion 24' and a pair of end flanges 27 and 29, with flange 27 being thicker than flange 29. The reel-like member 24 is a pressure applying and filler member of the portal and defines the reservoir chamber of the portal. The reel-like member 24 is inserted into the hollow interior of the main housing 20 after the silicone septum 22 has been inserted therein, such that the end flange 27 is inserted first so that it faces toward the septum 22, and toward the reduced opening 20' of the housing. The reel-like member 24 defines a first end opening 27' adjacent the end flange 27, which end opening 27' extends approximately three-fourths of the distance axially in the interior of the reel-like member 24, which hollow interior formed thereby constitutes the reservoir chamber or cavity 28 which allows access to the catheter 14 via the septum by a through hole 30 formed in a circumferential surface portion of the main housing 24'. Both the silicone septum 22 and the reel-like member 24 are positioned in the interior of the housing 20, and are forced therein via a conventional arbor press, such that the force thereby substantially compresses the septum 22 to fill the entire circumferential space of the interior of the housing 20 surrounding the septum, and to cause a slight projection of the upper surface face of the septum 22 through the reduced opening 20' of the housing 20. The housing 20 is provided with an inner annular bead at the end thereof adjacent to flange 21 which defines the space which the compressed septum 22 is to occupy, when compressed via the pressure-insert element 24. The beaded portion is of such width as to define a limit to the movement of the insert member 24 into the housing 20, thus providing a repeatedly-equal compression ratio for each septum 22 in each product manufactured. The beaded portion is indicated by reference numeral 47 in FIG. 5. The pressure typically used to compress the septum 22 via the reel-like member 24 is 2 to 3 pounds/in. With the septum 22 and reel-like member 24 in place in the interior of the housing 20 via the arbor press, the retaining ring 26 is thereafter inserted into the interior of the housing 20 directly adjacent the open end 20 thereof. The interior surface of the main housing 20 is provided with an annular groove directly adjacent the open end 20, and spaced therefrom an amount of approximately 1 mil., which groove also has a thickness of approximately 1 mil. With the arbor press still forcing the reel-like member 24 against the septum 22 to cause compression thereof, specially-designed retaining ring inserting pliers (not shown) is used for inserting the retaining ring 26 into the annular interior groove. The retaining ring 26 has a pair of plier-receiving openings 26' by which the specially-designed pliers may be inserted therethrough, for urging the two holes 26' toward each other for positioning the retaining ring within the annular groove, while the arbor press is still forcing the insert member 24 toward the septum 22 to cause the compression thereof. After the retaining ring 26 has been generally located coplanar with the annular groove on the interior surface of the main housing 20, the pair of pliers is removed from the holes 26' and the retaining ring is thereafter allowed to expand to thereby hold the member filler 24 in its compressing position against the septum 22, after which time the arbor press is released and removed from its operative engagement with the member 24.

The above-parts, 20, 22, 24, and 26, constitute the portal of the device 10. It is noted that prior to the assembly of the portal, as described above, the catheter 14 is first forced through the interior 27' of the filler 24 and thereafter through the through-opening 30, until such time as the other, second end of the catheter 14 is forced to abut against the interior surface of the member 24 via an enlarged beaded portion thereat, which prevents the passage of the second end of the catheter through the through-opening 30, to therby hold the second end of the catheter in place. After insertion of the catheter and abutment of the beaded portion of the second end of the catheter 14 against the inner-circumferential surface of the member 24, conventional medical glue is used to completely and fixedly bond the second end of the catheter to the interior surface of the member 24 around the through-opening 30. Toward this end, the inner circumferential surface of the member 24 is formed with a substantially rectilinearshaped recessed portion which surrounds the through-opening 30, such that the through-opening 30 lies within its boundary. This recessed rectilinear portion, which is preferably rectangular in shape, is of such length as to receive snuggly therein the beaded portion at the second end of the catheter 14, and which recessed rectilinear portion also receives the medical glue to surround the beaded portion of the second end of the catheter for providing a complete and strong bond therebetween to thereby fixedly connect the second end of the catheter to the portal via the interior surface of the recessed rectilinear portion of the interior of the member 24. It is noted that after the catheter 14 has been threaded through the through-opening 30, and after the medical glue used to bond the second end catheter to the interior surface of the of the member 24 has been applied, when the parts are assembled as described above, the transverse slot or groove 25 snugly receives therein and allows the projection therethrough of the catheter portion extending outwardly of the portal. In the completely assembled condition of the portal, the lower flange 29 of the member 24 fits snugly in the enlarged opening 20' of the main housing 20, and is retained therein via the retaining ring 26, as described above.

The other major portion of the device 10 is the silicone cuff 36, which includes a skirt portion 38 of substantially circular cross-sectional area, so as to define a truncated conical portion having an angularly sloped surface 38' of approximately between 10 and 15 degrees. The skirt portion 38 is a substantially solid portion and transforms into an upstanding, hollow tubular section 40 in which is received approximately the lower half of the main housing 20, with the other parts assembled therein, as shown in FIG. 5. The silicone cuff 36 also includes a protective bubble portion 37 which completely surrounds the end of the catheter 14 extending therethrough and also completely surrounds a protective stainless steel sheath or sleeve 42 which is telescopingly slid over the catheter 14 until it is adjacent the second end of the catheter connected to the portal. The silicone cuff 38 is also embedded with preferably five circular-shaped "Dacron" mesh reinforcing suture tabs or disks 50, with each tab preferably embedded in the silicone cuff 38 appoximately midway between the thickness thereof, as shown in FIGS. 2 and 3. The silicone cuff 38, along with the plurality of circular tabs 50, is used by the surgeon, when subcutaneously implanting the device, to affix the device to the patient's muscle fascia by non-absorbable sutures, with the tabs 50 reinforcing the sutures and preventing the removal of the device from the muscle fascia, as would occur if only the silicone cuff 38 were used for the fastening of the sutures. The use of a plurality of separate and distinct circular "Dacron" reinforcing tabs 50, as opposed to one continuous annular ring of supporting "Dacron" material used in prior art products, allows for a much easier method of forming the reinforcing means in the silicone cuff 38 during the molding and curing process, as described below in greater detail. Furthermore, since the angle of the skirt portion 38 is between approximately 10 and 15 degrees, as opposed to the prior art angles of between approximately 45 to 55 degrees, the amount of silicone needing penetration by the suture needle is considerably reduced, therefore making the fastening of the device to the muscle fascia a much easier task for the surgeon.

The end flange 27 of the element 24 also includes an axially-extending, raised, annular lip 27", which defines an inner hollow area receiving therein the lower face of the septum 22 to allow for ease of installation and to provide for the proper evenly-distributed forces for compression. The end flange 27 provides enough surface area against the lower face of the septum to provide this evenly-distributed compressive force against the septum.

The sloped portion 38' of the skirt 38 ends approximately midway between the flanges 27 and 29. All of the parts above-described, except for the silicone septum 22 and the cuff 36, are made of implantation grade, passivated stainless steel. The catheter beaded portion, or plug, at the second end thereof attached to the interior of the insert member 24, is made of medical grade silicone elastomer such as that manufactured by Dow Corning, MDX-4-4210. The plug itself is well known in the art and has been used in prior art infusion products.

Each of the stainless steel parts 20, 24, 26 and 42 are prepared for the type of quality allowing implantation into the body. All of the stainless steel components are cleaned with Freon TF and then passivated. The passivating solution is 20% $HNO_3$ (nitric acid) by volume, and the solution is heated to between 49 to 60 degrees Centigrade, after which each stainless steel component is added to the solution for 30 minutes and, thereafter, thoroughly rinsed in demineralized water. The suture reinforcing tabs 50 are made from "Silastic" sheeting, manufactured by Dow Corning Medical, which consists of a "Dacron" mesh embedded in silicone sheeting. The "Silastic" sheeting is prepared by washing it in distilled water and "Ivory" soap solution, and rinsed with distilled water, after which the five circular-shaped suture tabs are punched out with a stainless steel hole punch. Each circular suture reinforcing tab is then washed in 70% isopropyl alcohol for subsequent embedding into the silicone cuff during the molding process thereof, as described below in greater detail.

The septum is fabricated from a silicone elastomer mixture, which mixture is de-aired for 15 minutes at 29 degrees Hg to eliminate air bubbles. Thereafter, the elastic mixture is cleaned with freon solvent and placed in a 10 cc. syringe, and thereafter placed into an injection mold cavity where the remaining gas is allowed to escape. The mold's top plate is placed thereon, and the mixture is allowed to set for 60 seconds, after which time the mold is placed in an oven at 150 degrees Centigrade for 20 minutes, after which the material is ready for removal and for formation into a multitude of septa.

The final assembly of the device 10 is achieved in the following manner. After the components 20, 22, 24 and 26 have been assembled, as above described, and the catheter 14 has been attached to the assembled parts via the through-opening 30 and medical glue injected via a syringe to fixedly secure the second end of the catheter to the interior surface of the member 24 at the recessed, rectilinear portion, the entire assembly is placed into an injection mold for which the formation of the silicone cuff is to be achieved. After the assembled parts are placed into the mold, liquid silicone mixture, in a ratio of 10:1 base to catalyst ratio, is poured into the mold cavity after the mixture has been deaired in a vacuum for 15 minutes at 29 inches of Hg, or until air bubbles are evacuated. After the silicone mixture has been poured into the mold, such that it approximately reaches the height shown in FIG. 3 for the upper lip of the tubular section of the cuff, the individual circular reinforcing tabs 50 are embedded therein by using tongue depressors. During this stage, the benefit of using separate circular reinforcing tabs, each having a diameter of approximately 0.250 inches, is realized as opposed to the prior art technique of using one continuous annular ring of this material. In prior art techniques, the process of inserting the continuous annular ring into the liquid silicone mixture is a tedious task since, upon depressing one portion of the ring to immerse it in the liquid silicone mixture, another connected and adjacent portion thereof is forced to rise to the surface, owing to pressure waves created during the depressing procedure. Thus, to completely embed the annular ring is a very difficult and time consuming task. In the present invention, the use of separate circular reinforcing tabs 50 obviates this problem, since each tab is inserted using only one forcep, and it is a very simple task to place the tab midway of the height of the liquid silicone mixture, since there are no other closely connected portions thereof that might be affected by the pressure differentials.

After the separate circular reinforcing tabs 50 have been embedded in the liquid silicone mixture, the silicone mixture is allowed to level off and to have the gases escape. Thereafter, the mold lip is placed thereon and the mold, with its contents, is allowed to stand and cure for up to 24 hours at room temperature. The mold lid is then removed and the excess silicone is trimmed. At this point, the catheter may be cut to a desired standard length, such as 24 inches. Also at this stage, the upper lip of the tubular section 40 of the silicone cuff 36 is glued, using medical glue, to the exterior circumferential surface area of the main housing 20 to prevent the removal of the cuff 36 from the remainder of the assembly. The tubular portion is glued to the exterior surface of the housing via a bead of medical adhesive to form a seam between the inner surface of the tube 40 and the exterior surface of the housing 20. The finished product also includes the bubble portion 37 formed by the mold itself, which bubble portion 37 encloses therein the end of the catheter 14 directly adjacent and connected to the portal, as well as the protective sheath or sleeve 42, which sleeve 42 is in flush and abutting engagement against the circumferential surface portion of the main housing 20 directly adjacent thereto.

While a specific embodiment of the invention has been shown and described, it is to be understood that numerous changes, modifications and alterations thereof may be made without departing from the scope, spirit and intent of the invention, as set out in the appended claims, which constitute part of the disclosure hereof.

What is claimed is:

1. A subcutaneously implanted infusion device, comprising:
    a main housing of substantially hollow interior having a first end with an enlarged opening and a second end with a relatively smaller opening for mounting parts therein;
    a septum for mounting in said main housing adjacent said second open end of said main housing;
    a pressure-insert element for mounting in said main housing having a first substantially open end and a second closed end, the opening of said first end extending axially into the interior of said pressure-insert member to define an interior reservoir chamber, said first open end of said pressure-insert element abutting against the lower face of said septum for holding said septum in said main housing in a compressive state, said main housing having an inner annular groove formed along an inner circumferential surface thereof directly adjacent said enlarged opening of said first end of said main housing;
    a retaining clip for mounting in said annular groove formed in said main housing for holding said pressure-insert element therein for compressing said septum;
    said pressure-insert element comprising a through-opening along a circumferential portion thereof;
    a catheter having a first end and a second end, said catheter having a portion adjacent said second end extending through said through-opening of said pressure-insert element;
    means for fixedly connecting said second end of said catheter to said pressure-insert element, said second end of said catheter cooperating with said reservoir chamber of said pressure-insert element to thereby allow for communication between said catheter and said septum; and
    means for allowing fastening of said main housing by implantation within a subcutaneous opening in a human body, said means comprising an enlarged skirt portion, and a reduced-diameter hollow portion receiving therein at least a portion of said main housing, said enlarged opening of said main housing being positioned in said hollow portion of said means for allowing fastening.

2. The device according to claim 1, wherein said main housing further comprises a transversely extending slot having a first closed end and a second open end, said second open end lying flush with said enlarged opening of said main housing, whereby said transversely extending slot allows for the projection therethrough of a portion of said catheter extending from said second end of said catheter.

3. The device according to claim 1, wherein said pressure-insert element further comprises a first end flange adjacent said first substantially open end thereof, and a second end flange directly adjacent said second closed end of said pressure-insert element;
    said first end flange comprising an upstanding circular lip portion defining an interior circumference approximately equal to the circumference of said septum for snuggly receiving therein said septum, so that the lower face of said septum abuts against the substantially open end of said pressure-insert element.

4. The device according to claim 3, wherein said through-opening cooperates with the lower portion of said reservoir chamber closest to said second closed end of said pressure-insert element.

5. The device according to claim 1, wherein said retaining clip is C-shaped and comprises a first end having a first hole therein, and a second end having a second hole therein, said holes allowing for the insertion of a tool therein for compressing said retaining clip to allow for the insertion thereof in said annular groove.

6. The device according to claim 1, wherein said means for allowing fastening comprises a protective bubble portion extending outwardly from said hollow portion for encapsulating said portion of said catheter extending outwardly from said through-opening of said pressure-insert element.

7. The device according to claim 6, further comprising a protective metal sleeve for said portion of said catheter adjacent said second end thereof, said portion extending outwardly from said through-opening, said protective metal sleeve also being encapsulated by said bubble portion.

8. The device according to claim 1, wherein said main housing comprises a first end flange at said enlarged opening of said first end thereof, and a second end flange at said second end thereof.

9. The device according to claim 1, wherein said main housing further comprises an inner annular bead mounted adjacent said relatively reduced opening of said second end of said main housing, said annular bead preventing said pressure-insert element from passing beyond toward said relatively smaller opening of said second end.

10. The device according to claim 1, wherein said means for allowing fastening further comprises a plurality of spaced-apart, individual suture-reinforcing tabs embedded in said means between the top and bottom surfaces thereof.

11. The device according to claim 1, wherein said means for allowing fastening comprises an annular silicone cuff, wherein said skirt portion is a substantially frustro conical-shaped element having a surface slope of between 10 and 15 degrees, whereby the amount of material needing puncturing to allow for the suturing of the device to the muscle fascia is substantially reduced.

12. A subcutaneously-implanted infusion device comprising:
- a portal having therein a septum, and a reservoir chamber;
- a catheter having a first end fixedly connected to said portal and in fluid communication with said reservoir chamber;
- cuff means fixedly connected to at least a lower portion of said portal;
- a pressure-insert element having at least a partial hollow interior for defining said reservoir chamber, said pressure-insert element comprising at least one through-opening through which projects a portion of said catheter adjacent said first end thereof, said first end of said catheter being in fluid communication with said reservoir chamber defined by said pressure-insert element; and
- a protective catheter sleeve made of stainless steel, said protective catheter sleeve being telescopingly mounted about the portion of the catheter directly adjacent to and projecting from said through-opening of said pressure-insert element in order to protect said portion of said catheter adjacent said portal from it being punctured by a needle of a syringe, said cuff means comprising a protective bubble portion completely surrounding said protective metal catheter sleeve.

13. The device according to claim 12, wherein said cuff means further comprises a skirt portion having embedded therein a plurality of separate, spaced apart suture-reinforcing tabs, said skirt portion having a slope of between ten and fifteen degrees.

14. The device according to claim 12, wherein said portal comprises a main housing having an inner annular groove adjacent the end thereof mounted to said cuff means, and a C-shaped retaining ring mounted in said annular groove for retaining in said main housing said septum and said reservoir chamber of said portal for compressing said septum and for retaining said septum in its compressed state.

15. A subcutaneously implanted infusion device comprising:
- a portal comprising a main housing, a septum, and a pressure-insert element, said septum and said pressure-insert element being mounted within said main housing;
- said pressure-insert element having at least a partial hollow interior defining therein a reservoir chamber, said pressure-insert element also having a through-opening formed in one of the wall surfaces thereof to allow for fluid communication between said reservoir chamber and exteriorly thereof;
- a catheter having a first end portion fixedly connected to said pressure-insert element and passing through said through-opening thereof, and a second end remote from said first end for attachment to muscle fascia;
- cuff means fixedly connected to at least a portion of said main housing for providing a means by which said main housing is securable to muscle fascia;
- said main housing comprising a first end then a second end, said septum being positioned with said main housing adjacent said first end of said main housing;
- said main housing further comprising an inner annular groove adjacent said second end thereof, said pressure-insert element being positioned within said main housing between said inner annular ring and said septum; and
- a separable retaining ring mounted in said annular groove for retaining said pressure-insert element and said septum in said main housing, said retaining ring being substantially C-shaped in configuration.

16. The device according to claim 15, wherein said main housing further comprises an inner annular beaded portion positioned approximately adjacent to said first end of said main housing, and said pressure-insert element further comprising a first end flange member for abutting contact against said inner annular beaded portion to limit the insertion of said pressure-insert element into the interior of said main housing to thereby allow for a volume in which is positioned said septum.

17. The device according to claim 15, wherein said end flange member further comprises an upstanding rim having an inner diameter substantially equal to the outer diameter of said septum in its normal state, whereby the lower surface of said septum may be positioned on said first end of said pressure-insert element and surrounded by said annular rim.

* * * * *